United States Patent [19]
Amblard

[11] 3,943,363
[45] Mar. 9, 1976

[54] DEVICE FOR AUTOMATIC ANALYSIS MASS SPECTROMETRY

[75] Inventor: Jean-Claude Amblard, Vienne, France

[73] Assignee: Entreprise de Recherches et D'Activities Petrolieres Elf, Paris, France

[22] Filed: Sept. 17, 1974

[21] Appl. No.: 506,730

[30] Foreign Application Priority Data
Sept. 25, 1973 France .............................. 73.34263

[52] U.S. Cl. .................................. 250/288; 250/281
[51] Int. Cl.² .................... G01N 27/62; H01J 39/34
[58] Field of Search ........... 250/281, 288, 290, 291, 250/292, 293

[56] References Cited
UNITED STATES PATENTS
2,977,471  3/1961  Young et al. ........................ 250/288

FOREIGN PATENTS OR APPLICATIONS
979,958  1/1965  United Kingdom................. 250/281

*Primary Examiner*—James W. Lawrence
*Assistant Examiner*—T. N. Grigsby
*Attorney, Agent, or Firm*—Lane, Aitken, Dunner & Ziems

[57] ABSTRACT

Analysis of the composition of polyphase gas or liquid mixtures circulated continuously within pipe systems is carried out by withdrawing samples from primary circulation loops at regular intervals and passing them into a mass spectrometer connected to a computer for recording the results of analysis and controlling chemical processes which yield the different mixtures as effluents. Withdrawal and analysis of samples are performed in real time without any manual operation in order to permit adjustments of the unit in which the mixtures under analysis are circulated.

23 Claims, 4 Drawing Figures

DEVICE FOR AUTOMATIC ANALYSIS MASS SPECTROMETRY

This invention relates to a device for the automatic analysis by mass spectrometry of two-phase mixtures (gaseous and/or liquid mixtures) which circulate continuously within pipe systems.

In this device, the mass spectrometer is connected in real time to a computer which is employed both for recording the results of analysis and for controlling chemical processes which yield the different mixtures as effluents. This mass spectrometer serves especially to cary out analyses of effluents derived from the fractionating chains of a stream cracker in petrochemical processes or from a catalytic cracker in petroleum refining.

It is known that mass spectrometry is an extremely convenient and rapid means for performing accurate and rapid analyses of gas mixtures. In these spectrometers, the gas mixture to be analyzed is ionized, the different components having different masses being then separated in a magnetic prism in which the magnetic field $\vec{B}$ is perpendicular to the direction of the ionized particles. In the prior art, the spectrometer was connected to a computer but this was only for the analysis of spectra, the introduction being carried out either by hand or in a noncontinuous manner by means of samples taken from the different pipes in which the mixture was circulated; moreover, the operating parameters of the spectrometer were adjusted by hand. If it is desired to carry out continuous checking of the operating conditions of a steam-cracking unit, for example, it is important to check the composition of the various mixtures at regular intervals at precise points of the unit and to perform these checking operations in real time so that, by making use of the analytical results delivered by a printing machine connected to the computer (which counts the mass spectra produced by the analyzer), it is accordingly possible to modify certain settings of the unit in order to optimize the reactions which take place in the chemical treatment process. The parameters of the chemical reactions can equally well be adjusted automatically by the computer as a function of a program which utilizes the analytical results delivered by the device.

The present invention relates to a device for the automatic analysis by mass spectrometry of two-phase mixtures which circulate continuously within main pipes so as to permit quantity determination of the different compounds which circulate within a pipe, said pipe being chosen according to the indications given by the operator; these quantity determinations are performed at regular intervals and the results are indicated in a very short time.

In more exact terms, the device in accordance with the invention essentially comprises:

pipes constituting a plurality of primary loops $B_i$, each of said primary loops $B_i$ being connected to one of the main pipes and fitted with a flow regulating valve and a flowmeter in series;

pipes $T_i$, each of said pipes $T_i$ being such as to connect a branch point in a primary loop $B_i$ to a pneumatic valve $V_j$ through the intermediary of a dust filter $F_i$ and a needle valve for regulating the flow rate;

pneumatic valves $V_j$ for operably connecting one of the pipes $T_i$ to a traced pipe T';

a sampling cell at the extremity of the pipe T';

a sampling pipe T'' for connecting the outlet of the sampling cell to a recycling circuit through a delivery valve V' and a flowmeter in series;

means for measuring the pressure within the sampling cell;

means for regulating the pressure within the interior of the sampling cell by regulating th opening of the valve V' as a function of the difference between a value of the reference pressure and the pressure which is measured within the sampling cell;

a traced pipe T'''' for connecting the sampling cell to a pneumatic valve V'';

a capillary tube for connecting the pneumatic valve V'' to a chamber E;

pumping means for creating a vacuum within the chamber E;

a pipe for connecting the chamber E to the ionization chamber of a mass spectrometer;

electronic means for simultaneously initiating the application of voltage to the accelerating electrodes of the mass spectrometer and the opening of the pneumatic valve V'';

means for initiating the opening of the pneumatic valves $V_j$ according to the mixture of the gases to be analyzed.

In accordance with the invention, the first pneumatic valve $V_1$ which is connected to the two pipes $T_1$ and $T_2$ operably connects one of said two pipes to the pipe T'.

The mixtures to be analyzed are continuously circulated through the primary loops $B_i$ which are connected in parallel to the pipes employed for carrying said mixtures so that the sample withdrawn at the branch point should be representative of the mixture to be analyzed at the moment of analysis. The dusts filter removes the majority of fine solid particles entrained by the mixture; this filter is particularly essential in the analysis of the furnace effluents of a steam cracker since these latter contain a high proportion of small particles of solid carbon which would clog the different orifices of the device if they were not stopped by said filter. The pipes are traced or in other words fitted with a system for heating the external wall of the pipe in order that the compounds should remain gaseous at the pressure which prevails within the interior of said pipe. Tracing consists for example of an electrical resistance wire through which a current circulates as is the case with the tracing of the capillary tube according to the invention, that is to say a resistor which is wound with a variable pitch according to the quantity of heat which it is desired to supply to the pipe. Tracing can also consist of steam tracing and in this case the pipes are traced by winding a copper tube in which is circulated a fluid at high temperature such as steam, for example, said copper tube being wound around the pipe to be traced in a helix having a variable pitch.

The pipes can be traced by providing a sleeve made of a tube which is concentric with the pipe and in which is passed a fluid such as steam at high temperature, for example.

Regulation of the pressure of the sampling cell is performed by means of the valve V' which is controlled by a pressure regulator. The connection between the sampling cell and the mass spectrograph is established by means of a capillary tube connected to the outlet of a pneumatic valve which is fixed on the side of the cell and the inlet of which is in continuous communication with this latter. In accordance with the invention, said pneumatic valve V'' is operated simultaneously with the application of high voltage to the electrodes of the mass spectrometer. This makes it possible to prevent the ionization filament from being continuously swept by the gases outside periods of analysis and from being thus subject to premature wear. In accordance with the invention, the gases to be analyzed circulate in the vicinity of the filament only when it is desired to perform an analysis. The concentrations of various substances of the gaseous mixture which is injected into the sampling cell are obtained from selected peak heights in the spectrum produced by the mass spectrometer, by solving a system of linear equations whose coefficients result from calibration of the apparatus by means of pure substances.

If $P_k$ is the partial pressure of the constituent k per unit of pressure and $H_j$ is the height of the peak corresponding to the mass $j$ of the mixture, these two values are related by:

$$h_{kj} P_k = H_j.$$

The index $k$ varies from 1 to $m$ and the index $j$ varies from 1 to $n$. The coefficients $h_{kj}$ are measured by means of preliminary calibration of the apparatus. The heights of the peaks $H_j$ are measured by the mass spectrometer. The system of linear equations is solved as a function of the data $h_{kj}$ and $H_j$, thus giving the partial pressures $P_k$ which it is desired to know. The matrix is not necessarily a square matrix since a number of substances having different chemical configurations or even different chemical compositions but the same mass can contribute to a peak $H_j$ which corresponds to a predetermined atomic mass. In this case, the matrix is rectangular. The solution of these equations is performed in the computer which is associated with the mass spectrometer. The results of the analysis are printed. Depending on the results of this analysis and by comparing the concentrations of certain substances with analytical predictions obtained in accordance with the physical and chemical parameters of the apparatus in which the reactions are carried out, it is possible to modify these parameters in order to obtain enhanced efficiency of the apparatus.

In accordance with the invention, the mixture of compounds to be analyzed is selected and is circulated within one of the primary circulation loops $B_i$, in which the index $i$ varies from 1 to $N$; this selecting device essentially comprises:

a preselection key having two positions such that in the first position a direct-current voltage source is connected to N manual selection keys and that the direct-current voltage source is connected in a second position to the input of an automatic switch;

N manual selection keys each intended to establish a contact between the direct-current voltage source and one of the N leads which supplies said voltage to an array of electrovalves;

a switch for connecting the direct-current voltage source to one of the N leads aforesaid which constitute the N outputs of the switch controlled by the digital values applied to K inputs.

The value of K is higher than or equal to Log N/Log 2; in fact if there are N outputs, the selection of one of said N outputs is performed by means of a digital control which transcribes the number of said output in the binary system.

The invention further comprises an array of N −1 pneumatic valves $V_j$ of the slide-valve type and each having two inputs 1' and 2' and one output, said valves being connected in series in such a manner as to ensure that the output of the valve $j - 1$ is connected to the input 1' of the valve $j$, the traced pipe $T_j + 1$ being connected to the input 2' of the valve $j$, two electrovalves being adapted to control each pneumatic valve $V_j$, the first electrovalve being activated by the voltage supply lead $j + 1$ and adapted to control the lead which connects the output of the pneumatic valve to the input 2' of said valve $j$, the second electrovalve being adapted to control the lead which connects the input 1' to the output of the pneumatic valve $j$ when said second electrovalve is activated by any one of the supply leads 1 to $j$ and the output of the last pneumatic valve being connected to the traced pipe T'.

The first pneumatic valve $V_1$ which is connected to the two pipes $T_1$ and $T_2$ is controlled by two electrovalves, the first electrovalve which is activated by the lead 1 being adapted to couple the input 1' connected to the pipe $T_1$ to the output and the second electrovalve which is activated by the lead 2 being adapted to couple the input 2' connected to the pipe $T_2$ to the same output, said output being in turn coupled to the input 1' of the valve $V_2$.

By means of this arrangement of pneumatic valves and electrovalves, the mixture derived from one of the pipes $T_j$ is sent into the traced pipe T'. In the case of effluents to be analyzed which are at low pressure, a circuit is chosen through the multiple pneumatic valves of minimum length, especially when said effluents are liable to condense. In the case of light effluents such as hydrogen, they can be passed through all the electrovalves without any attendant difficulty or danger of condensation. This multiplexing system controlled by electrovalves makes it possible to connect to the traced pipe T' any one of the supply pipes through which the mixtures to be analyzed are circulated.

In one embodiment of the invention, the device is distinguished by the fact that a number of main pipes carrying the mixtures of products to be analyzed are under pressure; this is particularly the case when the mixtures to be analyzed are the effluents derived from fractionating chains of a steam cracker or a catalytic cracker.

In this case, the device in accordance with the invention is distinguished by the fact that all the pipes for the circulation of products under pressure to be analyzed are stainless steel tubes each fitted with an expansion valve on the downstream side and close to the point at which they are branched on the main duct.

The circulation pipes or tubes aforesaid are fitted with more or less complex systems according to the nature of the effluent to be transported.

If the sampling operation is performed in the gas phase and there is not attendant danger of condensation of certain components of the effluent at room temperature, the line is made up of a single stainless steel tube fitted with an expansion valve downstream of the point at which it is branched on the main duct. Said expansion valve is placed very close to the branch point in order to limit the pressure within the greater part of the tube (as a safety precaution); the expansion valve also makes it possible to set at a final and definite value the pressure to be maintained at the level of the analysis selection panel at the end of the line, taking into account the desired rate of flow within said line. Said analysis selection panel is constituted by the complete assembly of pneumatic valves and electrovalves employed for controlling the connection of a pipe $T_j$ to the traced pipe $T'$.

If the effluent is gaseous at the branch point but is subject to the danger of partial condensation at room temperature and at the operating pressure of the pipe, provision is made in accordance with the invention for steam tracing downstream of the expansion valve either by winding a copper tube around the stainless steel tube or by means of a sleeve which is swept by the steam.

If the effluent is gaseous but at very low pressure which is below the operating pressure of the selecting panel, a pumping system is necessary and located near the branch point if possible in order to employ the line as a pressure-variation filter. This filter is formed by the capacity of the line which integrates the pressure variations arising from the pumping system.

The fact of increasing the pressure can result in the appearance of condensates which are vaporized by tracing of the line.

If the effluent is liquid, the assembly in accordance with the invention is provided from the branch point with a vaporizer followed by an expansion valve and a traced pipe if necessary. If the pressure of the effluent is such that its temperature is close to the vaporization temperature of the liquid, the expansion valve performs the function of vaporizer on condition that the expansion is not liable to result in icing of said valve.

If the gaseous effluent contains compounds which condense at the temperature of the tracing steam at a pressure slightly higher than atmospheric pressure and solid particles (for example carbon derived from the cracking of naphtha), the supply line becomes more complex and more costly.

In the case just mentioned, said supply line is provided according to the invention with a system for sampling by means of loops, filters, heat exchangers and flash drums from which is delivered a mixture which remains gaseous at the tracing temperature. The flash drum employed is of the type described in French Pat. No. 7333933 of Sept. 21st, 1973.

In accordance with the invention, the device for controlling the mass spectrometer essentially comprises:

means for regulating the initial mass point of the analysis stream;

means for varying the velocity of sweeping of the magnetic field in the magnetic prism of the mass spectrometer.

Said sweeping velocity varies linearly or exponentially with time.

In the last-mentioned case of an exponential sweeping velocity, the width of the peaks of the spectrum delivered by the mass spectrometer remains constant throughout the analysis, that is to say irrespective of the position of the peaks within the spectrum at a given peak. At the same time, the interval between the peaks decreases exponentially. For a given analysis, the resolving power applies to the width of the peaks and not to the time of analysis, thereby facilitating the choice of an exponential sweep.

In a preferential embodiment of the invention, the output of the mass spectrometer comprises an electron multiplier connected in series with an amplifier $A_1$ having a low output impedance. The measurement signal derived from the electron multiplier at the output of the mass spectrometer is adapted by an amplifier having a very low output impedance in order to ensure that transmission of the analog signal to the measuring chain of the computer takes place under good conditions, that is to say without distortion of the signal.

In order to eliminate the multiple spurious components of 50 c/s frequency which interfere with the measurement signal, the device in accordance with the invention comprises an apparatus for integrating in 20 milliseconds connected in series after the output cable of the amplifier which has a low output impedance. The device in accordance with the invention is further distinguished by the fact that it comprises after the integrator:

an amplifier $A_2$ having a gain which is programmable according to the height of the peak;

a computer for storing the values of the heights of the peaks and the times of appearance of the peaks to be counted from the time of commencement of the sweep;

a printing unit for displaying the results of analysis obtained in real time and expressed in percentages by weight.

The computer further comprises couplers for transmitting logical control signals to the mass spectrometer and the selection panels and for recording the logical signals which transcribe the control signals delivered by the computer.

In accordance with the invention, the computer further comprises a device for controlling the operation of the analyzer, said device being controlled by a signal corresponding to any one of the following events:

a break in the filament which is the ion source of the analyzer;

failure of the high-voltage supply to the mass spectrometer;

insufficient vacuum within the mass spectrometer chamber;

absence of magnetic field in the mass spectrometer.

These different safety measures are useful for informing the operator immediately when one of the parameters of the measuring system attached to the mass spectrometer is defective.

The device in accordance with the invention is also distinguished by the fact that it comprises at least one clock for initiating at adjustable time intervals the successive analysis of a number of mixtures by controlling on the one hand the opening of suitable pneumatic valves and on the other hand the analytical cycle of the mass spectrometer.

Thus the request for analysis can be made either manually by depressing one of the function keys of the computer dialogue console and by specifying the number of the desired analysis, or automatically at predetermined clock times.

In order to comply with current safety standards in the petroleum and chemical industries, the device in accordance with the invention essentially comprises:

a pressurized enclosure containing the mass spectrometer, the associated electronic devices, and an air pressurizer (non-flameproof equipment);

the traced capillary tube which couples the sampling chamber to the mass spectrometer, which traverses one wall of the pressurized enclosure and connects the mass spectrometer to the sampling cell located in another ventilated enclosure;

the ventilated enclosure containing the pneumatic valves $V_j$, the electrovalves and the sampling pipes $T_j$.

In this manner, the delicate units such as the mass spectrometer and associated electronic equipment are separate from the pipes employed for supplying the different mixtures to be analyzed as well as from the different pneumatic valves. The two enclosures are connected together by the single capillary tube in which the gas flow rate is very low; in order to achieve enhanced safety, the room in which the delicate devices are located, is at a continuous excess air pressure in order that no explosible gas is liable to be introduced from the exterior into the pressurized enclosure.

A clearer understanding of the invention will in any case be gained from the following description of one exemplified embodiment of the invention which is given without any implied limitation, reference being made to the accompanying figures, in which.

As already mentioned in the foregoing, the invention consists in withdrawing samples of mixtures to be analyzed from primary circulation loops and sending said samples into a mass spectrometer, the withdrawal and analysis of said samples being performed in real time without any manual operation in order to permit the possibility of modifying the adjustments of the unit in which the different mixtures under analysis are circulated; this makes it possible to check the good operation of the unit and to optimize this latter; furthermore, an excessive or insufficient concentration of a substance facilitates identification of a defective apparatus.

Figure 1:
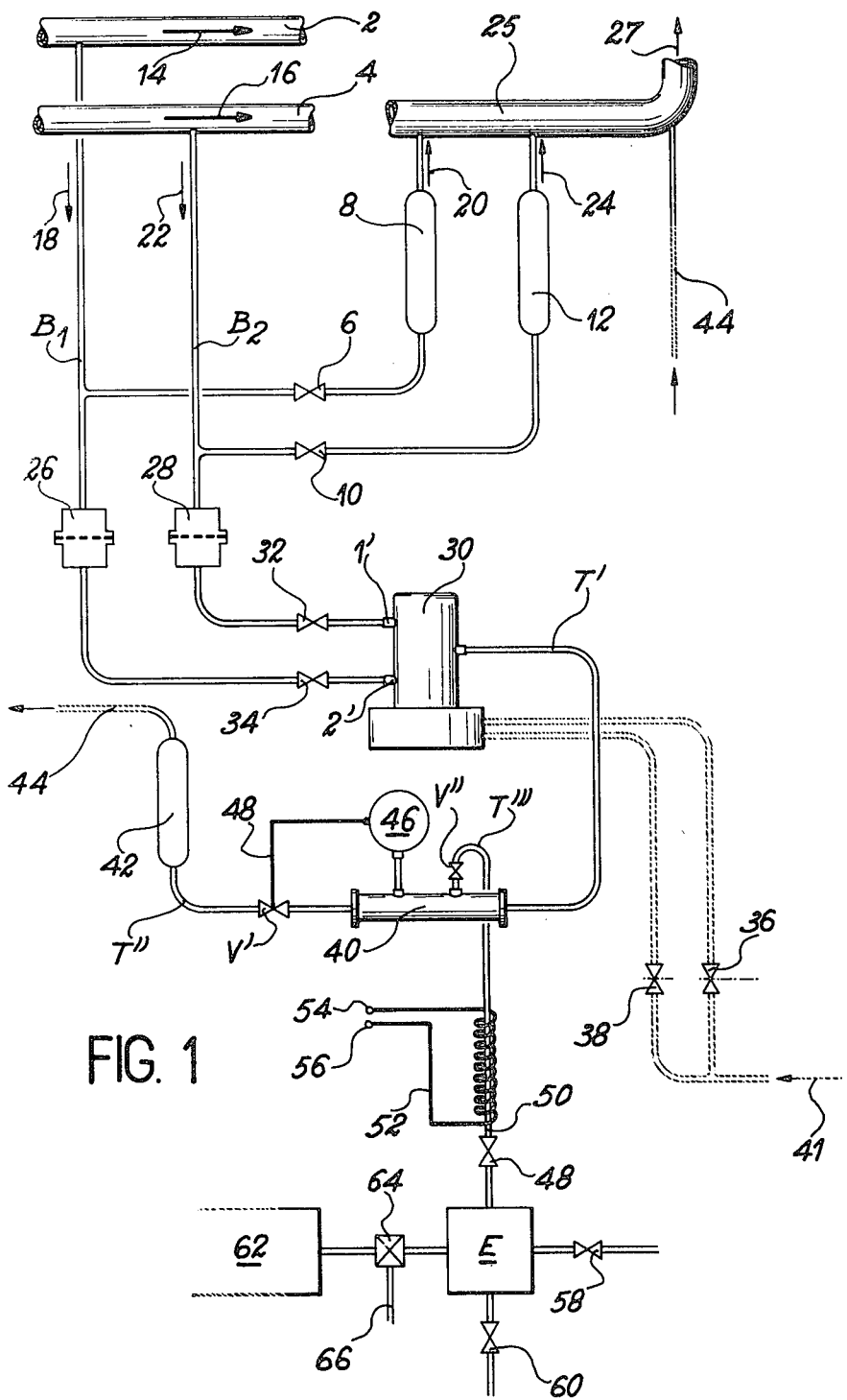
FIG. 1 is a diagram of the device according to the invention in which provision is made for two sampling loops.

There is shown in FIG. 1 a diagram of the sampling device which comprises main pipes 2 and 4 through which are circulated two mixtures to be subjected to analysis, a sampling loop $B_1$ connected in parallel to the pipe 2 and a sampling loop $B_2$ connected to the pipe 4, the sampling loop $B_1$ being fitted with the valve 6 and with the flowmeter 8 whilst the sampling loop $B_2$ is fitted with the valve 10 and with the flowmeter 12. The mixtures circulate within the different main pipes in the direction of the arrows 14 and 16. The mixtures circulate within the circulation loop $B_1$ in the direction of the arrows 18 and 20 and within the pipe $B_2$ in the direction of the arrows 22 and 24.

The primary loops and the pipe 44 are connected to a catchpot 25, the contents of which are recycled to the unit in the direction of the arrow 27. Each primary sampling loop is connected through filters such as the filters 26 and 28, then through valves such as the valves 32 and 34, to the inputs of a pneumatic valve 30. Said pneumatic valve connects either the input 1' or the input 2' to the pipe T' according to the control operation of the two electrovalves 36 and 38. The pneumatic valve 30 is of the so-called slide-valve type. When the valve 36 is activated, the input 1' of the pneumatic valve 30 is connected to the pipe T'; when the valve 38 is activated, the input 2' is connected to the output of the valve 30, that is to say to the pipe T'; the pipe T' connects the output of the pneumatic valve 30 to a sampling chamber 40. The gases under pressure are supplied to the pneumatic valve from a gas source (not shown) and circulate in the direction of the arrow 41.

The sampling chamber aforesaid is provided with an output connected to a pipe T'' which is fitted with a delivery valve V' and with a flowmeter 42. Said pipe T'' recycles or eliminates the different compounds which are directed into the sampling chamber 40 and circulate within the pipe 44. The sampling chamber 40 is equipped with an instrument 46 for measuring the pressure of gases within said sampling chamber 40. Said instrument 46 controls the opening of the valve V' by means of the electrical lead wire 48. The sampling chamber 40 is connected by means of the pipe T''' to a valve V'' which is in turn connected through a valve 48 to a chamber E via a capillary tube 50 traced by an electrical resistance wire 52 which is wound around the external surface of said tube. A voltage supply is applied to the terminals 54 and 56 of the electrical resistance wire 52.

The chamber E is equipped with pumping means (not shown in the figure) which are connected to said chamber E by means of valves 58 and 60. The same chamber E is connected to the ionization chamber 62 of the mass spectrometer through a valve 64 which also serves to measure in the branch 66 of said valve both the leakages and the pressure of gases within the interior of the ionization chamber and of the chamber E.

When it is desired to measure the composition of the mixture which circulates within the pipe 14, the valve 6 is adjusted so as to ensure a constant and representative flow rate within the loop $B_1$, whereupon the valve 34 is opened so that the inlet 2' of the pneumatic valve 30 is supplied with gas derived from the primary loop $B_1$; the electrovalve 38 is then activated and initiates the connection of the input 2' to the pipe T' of the pneumatic valve 30; the gas flow rate is adjusted within the sampling cell by means of the valve V' which is controlled by the pressure-measuring instrument 46; voltage is applied to the filament of the mass spectrometer at 62 and the valve V'' opens at the same time, with the result that part of the gas mixture which is present within the sampling chamber is sent into the chamber E. After a sufficient sweeping time, the magnetic field is set up within the mass spectrometer (which is not shown in detail in the figure) in order to analyze the various components of the mixture having different masses.

Figure 2:
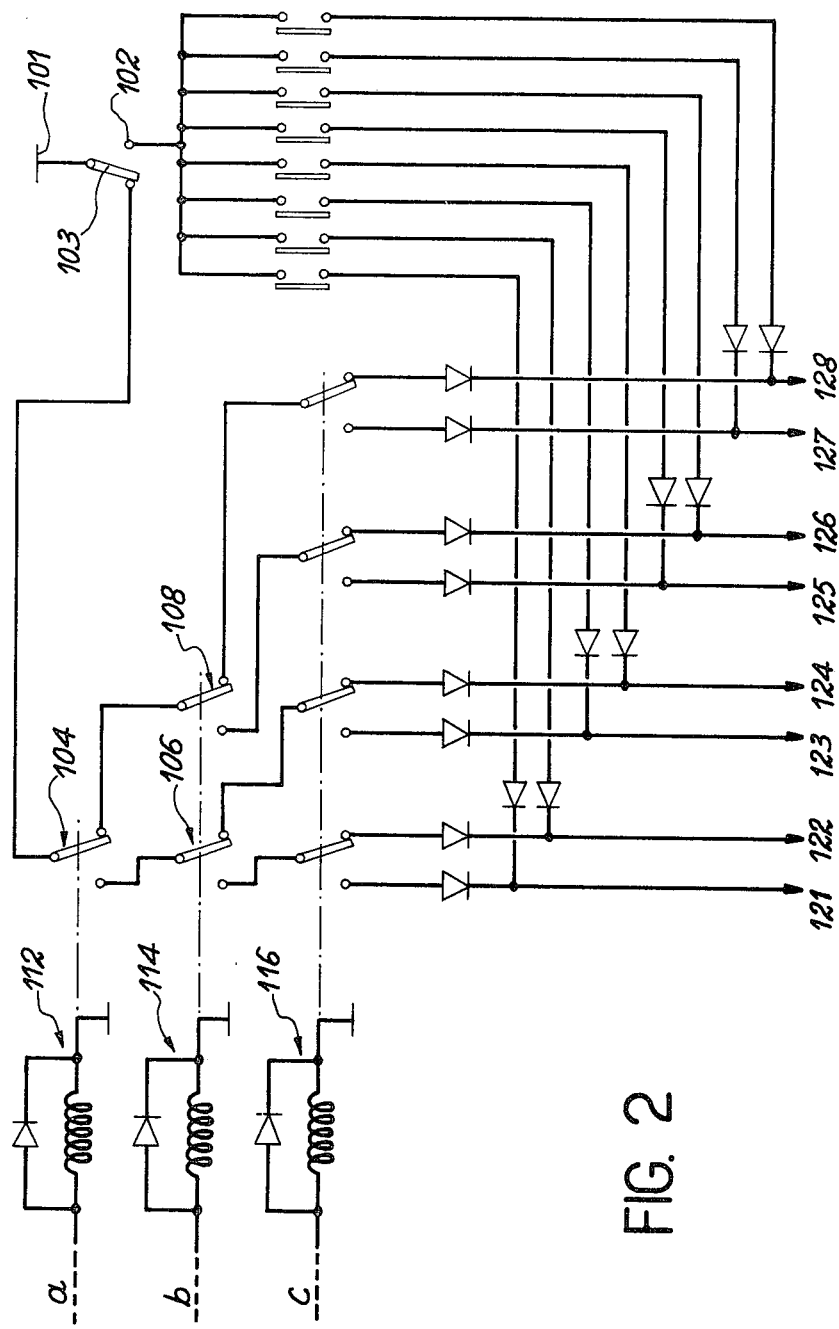
FIG. 2 is a diagram of the electrovalve control panel comprising eight power supply leads.

FIG. 2 shows the electronic circuit arrangement for controlling the different electrovalves. A d.c. voltage source is connected to the terminal 101; a preselection key 103 connects said d.c. voltage source either to an array of eight leads in the case of manual control in which case the connection is made when the key is connected to the terminal 102 or to a set of relay contacts such as those designated by the reference numerals 104, 106, 108 and so forth, said contacts being connected in a series-parallel circuit arrangement. These contacts are controlled by electromagnets designated by the reference numerals 112, 114 and 116. When all these electromagnets are activated, the connections are established as shown in FIG. 2. The automatic selection system connects one of the eight arms of the circuit consisting of current supply leads designated by the reference numerals 121, 122, 123, 124, 125, 126, 127 and 128 to the d.c. voltage source 108. In the case of FIG. 2, it is the lead 128 which is connected to the key 101. Depending on the digital values 0 or 1 applied to the coils of the electromagnets which control the relays such as 106, 108, the connection between the voltage at 101 and one of the leads is established in accordance with the rules laid down by the following truth table in which the digital values are applied at $a$, $b$ and $c$.

| a | b | c | channel |
|---|---|---|---------|
| 0 | 0 | 0 | 121 |
| 0 | 0 | 1 | 122 |
| 0 | 1 | 0 | 123 |
| 0 | 1 | 1 | 124 |
| 1 | 0 | 0 | 125 |
| 1 | 0 | 1 | 126 |
| 1 | 1 | 0 | 127 |
| 1 | 1 | 1 | 128 |

Under manual control, the relay 103 connects the terminal 101 to the terminal 102. One of the eight manual selection keys serves to connect one of the eight supply leads and only one of the eight leads to the terminal 102 which is in turn connected to the d.c. voltage source 101.

Figure 3:
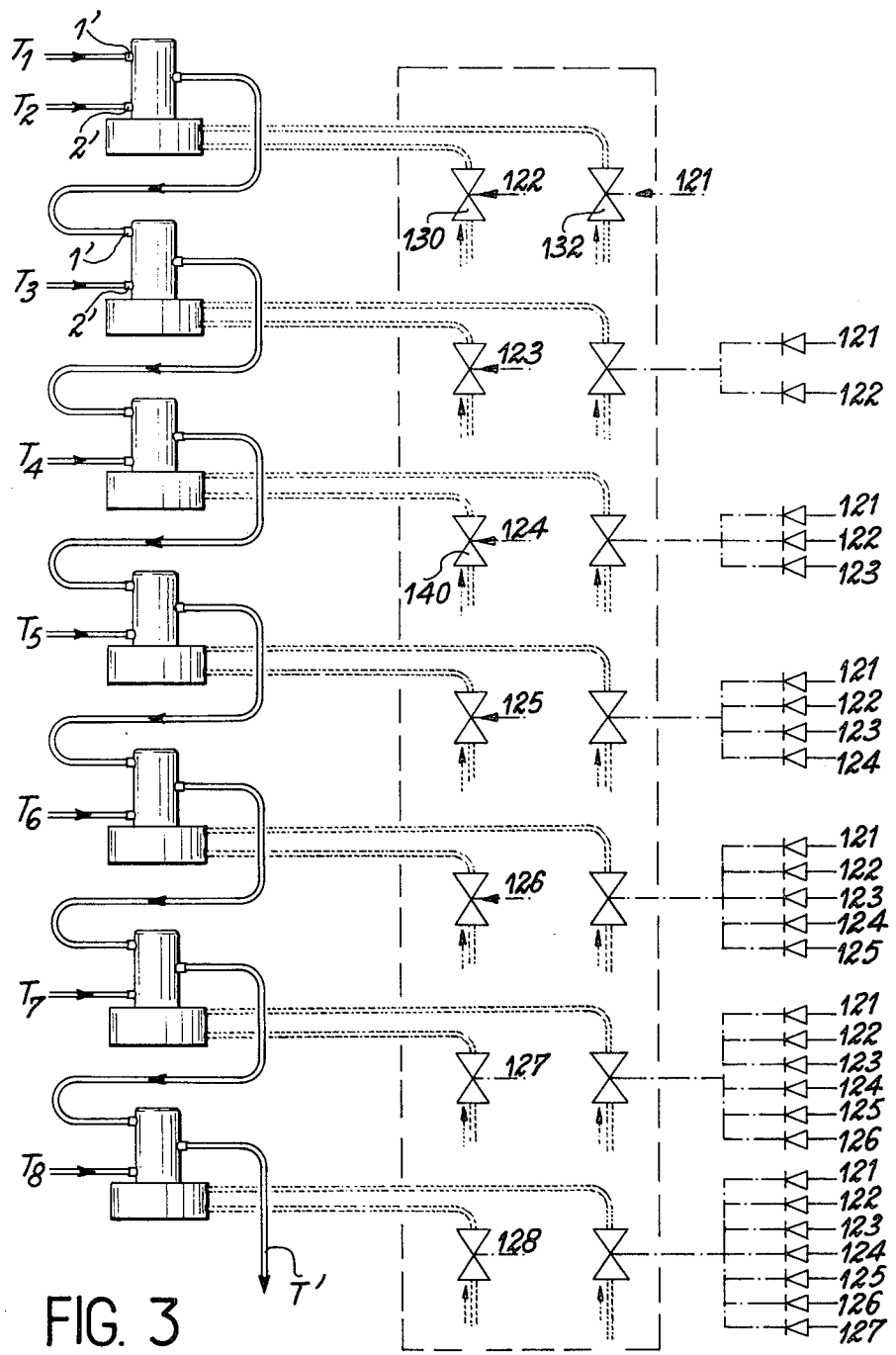
FIG. 3 is a diagram of the device for controlling the pneumatic valves by means of electrovalves and voltage supplies.

There is shown in FIG. 3 the array of seven pneumatic valves which serve to connect to the pipe T' one of the eight inputs connected to the pipes $T_1$, $T_2$, $T_3$, $T_4$, $T_5$, $T_6$, $T_7$, $T_8$. Pairs of electrovalves such as 130 and 132 control the connection of the inputs 1' or 2' to the outputs of the pneumatic valves. The output of each pneumatic valve is connected to the input 1' of the adjacent pneumatic valve. The electrovalves which control the connection of the outputs of the pneumatic valves to the inputs such as 2' are connected to the supply leads 122, 123, 124, 125, 126, 127 and 128. The valves such as the valve 132 which connect the inputs such as 1' to the outputs of the pneumatic valves are connected to all the leads corresponding to the electrovalves of lower order in the series. Thus the manual control, for example, of the key which connects the voltage terminal 101 to the supply lead 124 of FIG. 2 energizes the electrovalve 140 which is connected to the lead 124, with the result that the pipe $T_4$ is connected to the output of the third pneumatic valve. As a result of the energization of all the following electrovalves, namely those which connect the inputs 1' to the outputs of the pneumatic valves, the gases circulated within the pipe $T_4$ pass through the following four pneumatic valves and terminate in the pipe T'.

It is apparent that in the particular example of eight channels which has just been given, it is thus possible to initiate the connection of the valve T' to any one of the pipes from $T_1$ to $T_8$. In order that the gases to be analyzed should not pass through an excessive number of pneumatic valves, it is sometimes an advantage to group the pneumatic valves together in parallel branches. Accordingly, if it is desired to carry out the quantity determination of gas derived from 32 pipes $T_1$ to $T_{32}$, it is an advantage to assemble the pneumatic valves in series in groups of eight, that is to say to place four series of eight pneumatic valves connected in parallel to a single outlet pipe T'.

Figure 4:
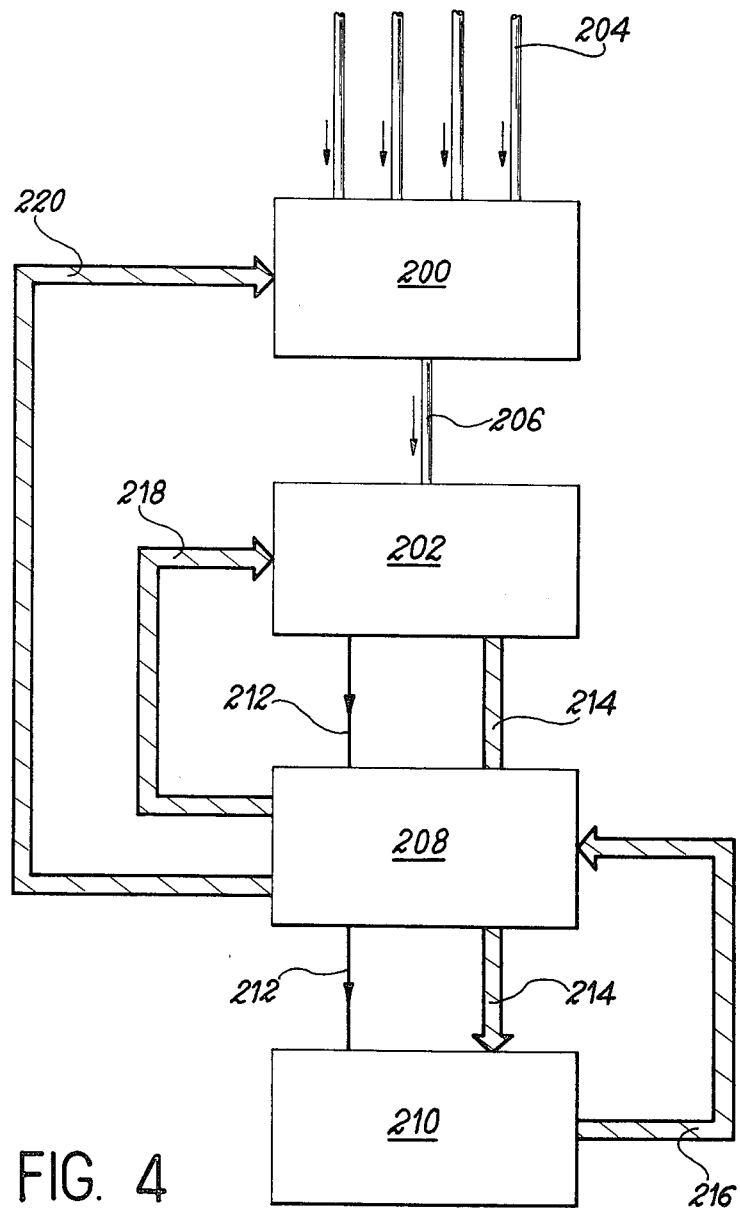
FIG. 4 is a diagram of the complete system.

In FIG. 4, there is shown a diagram of the complete system comprising a sampling panel 200 for directing to the mass spectrometer 202 a gaseous effluent such as the effluent carried by the pipe 204 and derived from one of the branch points connected to said panel; the mass spectrometer is equipped with a device for continuously introducing gas to be analyzed as described earlier and indicated by the arrow 206. An electronic interface 208 ensures adaptation of information in the direction of computer to mass spectrometer and conversely; the digital computer 210 carries out all the control operations defined in the foregoing in the direction of the three assemblies, namely the sampling panel, the mass spectrometer and the interface; said computer serves to obtain and process the spectra and to control the good operation of the mass spectrometer. The arrow 212 which connects the mass spectrometer to the computer carries an electrical signal which is proportional to the height of the peaks: this is the measurement signal; the arrow 214 which proceeds from the mass spectrometer to the computer through the interface represents the communication of the mass spectrometer cutoff signals to the computer. The arrow 216 represents the leads which establish a communication between the digital outputs derived from the computer and the interface, which are brought out of said interface and passed to the mass spectrometer in the direction of the arrow 218 for a sequential control of the mass spectrometer and in the direction of the arrow 220 towards the sampling panel 200 for a sequential control of said panel.

The example of construction as described below relates to the steam cracker which is installed in the ELF refinery at Feyzin, France. The system comprises two series of pneumatic valves, one series being made up of eight analytical channels and the other series being made up of six analytical channels. The nature of the charge of the steam cracker is naphtha (light gas oil) and ethane derived from the fractionation of the cut $C_2$. The cuts C which are followed by a numeral denote pipes in each of which is circulated a gas mixture containing the same number of carbon atoms in each component of the mixture as the numeral which follows the letter C of the cut. Accordingly, the gases which have two carbon atoms, namely acetylene, ethylene and ethane, are circulated in the cut $C_2$.

The twelve possible analyses within the twelve channels are analyses of:

1. the cut $C_2$ prior to passing into the hydrogenation reactors;
2. the cut $C_2$ after passing into the hydrogenation reactors;
3. the hydrogen gas prior to Joule-Thomson expansion;
4. the hydrogen gas after Joule-Thomson expansion;
5. the gas supplied to the steam cracking furnaces;
6. the gas produced by the Feyzin plant;
7. the gas exported by the steam cracking reactor;
8. the cut $C_3$ upstream of the hydrogenation reactor;
9. the flare gas of the unit;
10. the light gasoline of the hydro-treatment section;
11. the intermediate gasoline of the hydro-treatment section;
12. the effluents which pass out of the cracking furnaces.

Analyses 1, 2, 3, 4, 5, 6 and 7 entail the use of single lines each equipped with an expansion valve located behind the branch point. The pressure attains 25 bars in certain branch points. Analysis 8 calls for a single line with expansion valve and heater. The expansion must be fractionated owing to the very high pressure at the branch point which would result in icing of a single expansion valve.

Analysis 9 entails the need for a line traced with steam and for a pump, the flare pressure being lower than the operating pressure of the sampling panels. Coupling of analyses 10 and 11 is carried out by means of traced lines each fitted with an expansion valve. Analysis 12 calls for the installation of a special sampling system, namely the flash drum described in French Pat. application No. 7333933.

The pressure at the pneumatic-valve inlets is 1.3 bar relative, that is to say 1.3 bar above atmospheric pressure. The regulated pressure within the sampling cell is 70 g/cm². The gas flow rate within the sampling cell is approximately 12 liters per minute. The flow rate within the capillary sampling tube is 1 to 2 liters per minute and the resolving power chosen for the mass spectrometer in the case of these values of flow rate is 300. This value is sufficient for the quantity determination of substances from hydrogen to naphthalene. The duration of the analyses is 45 seconds in the case of the cuts $C_2$ and two minutes in the case of the effluents at the outlet of the furnace. The accuracy of the measuring chain is $2.5 \times 10^{-4}$.

What we claim is:

1. A device for the automatic analysis by mass spectrometry of polyphase mixtures which circulate continuously within main pipes, wherein said device comprises:

pipes constituting a plurality of primary loops ($B_i$), each of said primary loops ($B_i$) being connected to one of the main pipes and fitted with a flow regulating valve and a flowmeter in series;

pipes ($T_i$), each of said pipes ($T_i$) being such as to connect a branch point in a primary loop ($B_i$) to a pneumatic valve ($V_j$) through the intermediary of a dust filter ($F_i$) and a needle valve for regulating the flow rate;

pneumatic valves ($V_j$) for operably connecting one of the pipes ($T_i$) to a pipe ($T'$);

a sampling cell at the extremity of the pipe ($T'$);

a sampling pipe ($T''$) for connecting one outlet of the sampling cell to a recycling circuit through a delivery valve ($V'$) and a flowmeter in series;

means for measuring the pressure within the sampling cell;

means for regulating the pressure within the interior of the sampling cell by regulating the opening of the valve ($V'$) as a function of the difference between a value of the reference pressure and the pressure which is measured within the sampling cell;

a traced pipe ($T'''$) for connecting the sampling cell to a pneumatic valve ($V''$);

a capillary tube for connecting the pneumatic valve ($V''$) to a chamber (E);

pumping means for creating a vacuum within the chamber (E);

a pipe for connecting the chamber (E) to the ionization chamber of a mass spectrometer;

electronic means for simultaneously initiating the application of voltage to the accelerating electrodes of the mass spectrometer and the opening of the pneumatic valve ($V''$);

means for initiating the opening of the pneumatic valves ($V_j$) according to the mixture to be analyzed.

2. A device according to claim 1, wherein said device comprises means for ensuring that the first pneumatic valve ($V_1$) which is branched on the two pipes ($T_1$ and $T_2$) operably connects one of said two pipes to the traced pipe ($T'$).

3. A device according to claim 1 for selecting the mixture of compounds to be analyzed which is circulated within one of the primary circulation loops ($B_i$ in which the index $i$ varies from 1 to N), wherein said device comprises:

a preselection key having two positions such that a direct-current voltage source is connected in the first position to N manual selection keys and that said direct-current voltage source is connected in a second position to the input of an automatic switch;

N manual selection keys each intended to establish a contact between the direct-current voltage source and one of the N leads which supplies said voltage to an array of electrovalves;

a switch for connecting the direct-current voltage source to one of the N leads aforesaid which constitute the N outputs of the switch controlled by the digital values applied to K inputs;

an array of N–1 pneumatic valves ($V_j$) of the slide-valve type and each having two inputs (1' and 2') and one output, said valves being connected in series in such a manner as to ensure that the output of the valve ($j$–1) is connected to the input (1') of the valve ($j$) the traced pipe ($T_{j+1}$) being connected to the input (2') of the valve ($j$), two electrovalves being adapted to control each pneumatic valve ($V_j$), the first electrovalve being activated by the voltage supply lead ($j$+1) and adapted to control the lead which connects the output to the input (2') of said pneumatic valve ($j$), the second electrovalve being adapted to control the lead which connects the input (1') to the output of the pneumatic valve ($j$) when said electrovalve is activated by any one of the supply leads (1 to $j$) and the output of the last pneumatic valve being connected to the traced pipe ($T'$).

4. A device according to claim 3, wherein the first pneumatic valve ($V_1$) which is connected to the two pipes ($T_1$ and $T_2$) is controlled by two electrovalves, the first electrovalve which is activated by the lead (1) being adapted to couple the input (1') connected to the pipe ($T_1$) to the output and the second electrovalve which is activated by the lead (2) being adapted to couple the input (2') connected to the pipe ($T_2$) to the same point, said output being in turn coupled to the input (1') of the valve ($V_2$).

5. A device according to claim 1 wherein the main pipes for the circulation of mixtures of products to be analyzed are under pressure.

6. A device according to claim 5 for sampling and analysis of gaseous products at room temperature, wherein all the pipes for the circulation of said products are stainless steel tubes each fitted with an expansion valve on the downstream side and close to the point at which they are branched on the main duct.

7. A device according to claim 5 for sampling and analysis of products which are liquid at room temperature after passing through the expansion valve, wherein all the pipes for the circulation of said products are traced at a temperature such that said products are in the gas phase.

8. A device according to claim 5 for sampling gaseous products at low pressure, wherein said device comprises means for pumping said products in the vicinity of the branch points in the main pipes and directing said products under pressure into the primary circulation loops ($B_i$).

9. A device according to claim 5 for the analysis of liquid products, wherein the traced pipes corresponding to said sampling operation comprise a vaporizer in the pipe ($B_i$) near the branch point.

10. A device according to claim 1, wherein the pipes are traced by winding a copper tube in which a fluid at high temperature is circulated, said copper tube being wound around the stainless tube with a variable winding pitch.

11. A device according to claim 1, wherein a fraction of each pipe is traced by placing a sleeve formed of a tube which is concentric with said pipe, said sleeve being swept by a fluid at high temperature.

12. A device according to claim 10, wherein the fluid at high temperature is steam at high pressure.

13. A device according to claim 1 wherein a fraction of each pipe passes through a flash drum located upstream of the mass spectrometer.

14. A device according to claim 1 wherein the device for controlling the mass spectrometer comprises:
means for regulating the initial mass point of the analysis stream;
means for varying the velocity of sweeping of the magnetic field in the magnetic prism of the mass spectrometer.

15. A device according to claim 14, wherein said device comprises means for varying the sweeping velocity linearly with time.

16. A device according to claim 14, wherein said device comprises means for varying the sweeping velocity exponentially with time.

17. A device according to claim 14, wherein the output of the mass spectrometer comprises an electron multiplier connected in series with an amplifier ($A_1$) having a low output impedance.

18. A device according to claim 17, wherein said device comprises an integrator in series after the output cable of the amplifier ($A_1$).

19. A device according to claim 18, wherein said device comprises after the integrator:
an amplifier ($A_2$) having a gain which is programmable according to the height of the peak corresponding to the mass of one of the analyzed products;
a computer for storing the values of the peaks and the instants of appearance of said peaks;
a printer for displaying the results of analysis obtained in real time.

20. A device according to claim 19, wherein the computer comprises a unit for recording and indicating the all-or-none logical signals corresponding to stoppage of sweeping of the mass spectrometer.

21. A device according to claim 19 wherein the computer comprises a cut-off circuit for interrupting the storage of data, said circuit being controlled by a signal corresponding to any one of the following events:
a break in the source filament;
a failure of the high-voltage supply to the mass spectrometer;
insufficient vacuum within the mass spectrometer chamber;
absence of magnetic field in the mass spectrometer.

22. A device according to claim 1 wherein said device comprises at least one clock for initiating at adjustable time intervals the successive analyses of a number of mixtures by controlling the opening of suitable pneumatic valves and the analytical cycle of the mass spectrometer.

23. A device according to claim 1 wherein said device comprises:
a pressurized enclosure containing the mass spectrometer, the associated electronic devices and an air pressurizer;
the traced capillary tube which traverses one wall of the pressurized enclosure and connects the mass spectrometer to the sampling cell located in another ventilated enclosure;
the ventilated enclosure containing the pneumatic valves ($V_j$), the electrovalves and the sampling pipes ($T_j$).

* * * * *